(12) United States Patent
Carella et al.

(10) Patent No.: US 8,211,705 B2
(45) Date of Patent: Jul. 3, 2012

(54) ELECTRICAL DETECTION AND QUANTIFICATION OF MERCURIC DERIVATIVES

(75) Inventors: Alexandre Carella, Mazeres Lezons (FR); Jean-Pierre Simonato, Sassenage (FR)

(73) Assignee: Commissariat a l'Energie Atomique Et Aux Energies Alternatives, Paris (FR)

( * ) Notice: Subject to any disclaimer, the term of this patent is extended or adjusted under 35 U.S.C. 154(b) by 302 days.

(21) Appl. No.: 12/724,741

(22) Filed: Mar. 16, 2010

(65) Prior Publication Data

US 2010/0255593 A1    Oct. 7, 2010

(30) Foreign Application Priority Data

Mar. 18, 2009 (FR) ...................................... 09 01252

(51) Int. Cl.
*G01N 33/20* (2006.01)
*G01N 27/00* (2006.01)

(52) U.S. Cl. ..................... 436/81; 422/82.02; 422/82.03; 422/82.01; 422/98; 977/742; 977/762; 204/418; 204/290.05; 204/290.11; 204/416

(58) Field of Classification Search .................. 436/81; 422/82.02, 82.03, 82.01, 98; 977/742, 762; 204/418, 290.05, 290.11, 416
See application file for complete search history.

(56) References Cited

U.S. PATENT DOCUMENTS

| | | | | |
|---|---|---|---|---|
| 4,352,726 A | * | 10/1982 | Sugano et al. | 204/413 |
| 5,133,856 A | * | 7/1992 | Yamaguchi et al. | 204/416 |
| 5,874,039 A | * | 2/1999 | Edelson | 313/310 |
| 6,200,444 B1 | | 3/2001 | Ahlers et al. | |
| 6,436,259 B1 | * | 8/2002 | Russell | 204/418 |
| 2005/0006623 A1 | | 1/2005 | Wong et al. | |
| 2006/0284169 A1 | | 12/2006 | Park et al. | |

FOREIGN PATENT DOCUMENTS

| | | |
|---|---|---|
| GB | 2 030 358 | 4/1980 |
| WO | WO 2009/039298 | 3/2009 |

OTHER PUBLICATIONS

Zhu Mei et al., "Visible Near-Infrared Chemosensor for Mercury Ion," *Organic Letters*, vol. 10, No. 7, pp. 1481-1484; 2008.
Wang Hung-Ta et al., "Fast electrical detection of Hg(II) ions with AlGaN/GaN high electron mobility transistors," *Applied Physics Letters*, AIP, American Institute of Physics, vol. 91, No. 4, pp. 42114-4-42114-3, Jul. 27, 2007.
Ungureanu et al., "Preliminary Tests for N,N-Diethylaniline Grafting on Carbon Nanotubes," *Revistas De Chimie*, vol. 58, No. 9, pp. 866-870, 2007.
Search Report for Application No. FR 0901252 dated Oct. 20, 2009.

* cited by examiner

*Primary Examiner* — Robert J Hill, Jr.
*Assistant Examiner* — Dwan A Gerido
(74) *Attorney, Agent, or Firm* — Alston & Bird LLP

(57) ABSTRACT

The invention relates to an apparatus and to a method for detecting and/or quantifying mercuric ions, $Hg^{2+}$. The apparatus of the invention is of the type comprising an electrical device comprising two electrodes and a substrate comprising at least one surface made of an organic or inorganic semiconductor material, the electrodes being in electrical contact with said organic or inorganic semiconductor material, and a device for measuring the variation in the conduction current between the two electrodes, and wherein at least one compound which complexes mercuric ions $Hg^{2+}$, selected from a dithia-dioxa-monoaza crown ether compound, an N,N-di(hydroxyethyl)amine, an N,N-di(carboxyethyl)amine, and mixtures of two at least of these compounds, is bonded to said semiconductor material or to an electrode of said electrical device. The invention finds application in the field of the detection of mercuric ions, in particular.

19 Claims, No Drawings

ELECTRICAL DETECTION AND QUANTIFICATION OF MERCURIC DERIVATIVES

CROSS REFERENCE TO RELATED APPLICATION

This application claims priority from French Application No. 09/01252, filed Mar. 18, 2009, which is hereby incorporated herein in its entirety by reference.

The invention relates to an apparatus and to a method for detecting and quantifying mercuric ions, $Hg^{2+}$.

BACKGROUND

It is well known that mercury is a toxic and/or ecotoxic compound in all of its organic forms and in respect of all of its chemical states.

The reason is that mercury accumulates within organisms and is the cause of numerous diseases, affecting particularly the kidneys, the digestive system, and the neurological system.

Of all the oxidation states, it is the ions of mercury II, $Hg^{2+}$, that are the most toxic.

The development of selective sensors for this element is of particular interest for the purposes of quantifying and detecting this element in the natural environment, water, and foods.

Moreover, determining the concentration of mercury in water intended for food use is necessary within the context of regulations concerning drinking water and concerning hazardous materials.

The technique used at present for quantifying mercury in water is that of atomic absorption spectroscopy.

This technique, although accurate and reliable, has a number of drawbacks.

In particular, it involves heavy equipment which is difficult to transport.

Mercuric compounds may also be detected using selective fluorescent and colorimetric sensors, by grafting chromophores or fluorophores onto dithia-dioxa-monoaza crown ether compounds.

The dithia-dioxa-monoaza crown ether compounds complex the $Hg^{2+}$ ions selectively, and this complexation produces a change in the properties of the chromophores or fluorophores bound to them.

This change in optical properties of the chromophores or of the fluorophores is due to an electron-attracting effect of the mercury, which depletes the chromophore.

Accordingly, Zhu et al. in Org. Lett., 2008, 10, 1481-1484, propose a chemical sensor for mercuric ions $Hg^{2+}$, in which a dithia-dioxa-monoaza crown ether compound, to which a tricarbocyanine dye is grafted, is used to complex the $Hg^{2+}$ ions, and thus causes a change in color of the dye when the $Hg^{2+}$ ions are complexed by the crown ether.

This change in color is visible to the naked eye.

However, this technique does not allow the detection of small quantities of $Hg^{2+}$ ions and, moreover, does not allow the concentration of $Hg^{2+}$ in the sample under analysis to be determined.

The same document indicates that the detection of mercuric ions $Hg^{2+}$ may also be accomplished by analyzing the fluorescence emitted by the dye grafted onto the crown ether.

This technique, apart from the impossibility of determining the concentration of $Hg^{2+}$ ions, has the drawback of having to be performed under reduced-light conditions, and this does not allow it to be performed directly on site.

U.S. Pat. No. 7,385,267 B2 describes electrical devices in which nanotubes or nanowires of a conductor material are functionalized with a molecule which undergoes a change in property on contact with an analyte for detecting within a sample.

This device allows the analyte in the sample to be detected by detecting the change in property of the conductor material.

There is no reference in that document to the detection of $Hg^{2+}$ ions or to the modification of the conduction properties of a semiconductor material grafted with a compound which complexes mercuric ions $Hg^{2+}$ when contacted with the $Hg^{2+}$ ions.

Accordingly, a need exists for an apparatus for detecting and/or quantifying $Hg^{2+}$ ions that are present in gaseous form or in solution in water or in an unknown solvent, it being possible for said apparatus to be used on site, irrespective of the light conditions, and to be transportable.

SUMMARY

To this end, the invention provides an apparatus for detecting and/or quantifying mercuric ions $Hg^{2+}$, of the type comprising:

an electrical device comprising two electrodes and a substrate comprising at least one surface made of an organic or inorganic semiconductor material, the electrodes being in electrical contact with said organic or inorganic semiconductor material, and a device for measuring the variation in the conduction current between the two electrodes, wherein at least one compound which complexes mercuric ions $Hg^{2+}$, selected from a dithia-dioxa-monoaza crown ether compound, an N,N-di(hydroxyethyl)amine, an N,N-di(carboxyethyl)amine, and mixtures of two at least of these compounds, is grafted onto said semiconductor material or onto an electrode of said electrical device.

DETAILED DESCRIPTION

In a first embodiment of the apparatus for detecting and/or quantifying mercuric ions $Hg^{2+}$ of the invention, the substrate of the electrical device is entirely composed of an organic or inorganic semiconductor material.

In a second, more particularly preferred embodiment of the apparatus for detecting and/or quantifying mercuric ions $Hg^{2+}$ according to the invention, the substrate of the electrical device comprises a silica ($SiO_2$) support covered with a semiconductor material.

The semiconductor material of the substrate of the device is preferably selected from a material based on carbon, silicon, germanium, zinc, gallium, indium, cadmium, or mixtures of two at least thereof.

A material based on carbon, silicon, germanium, zinc, gallium, indium, cadmium, or mixtures of two at least thereof is a material containing at least 20 mol % of carbon, of silicon, etc., relative to the total number of moles of compound in the material.

More preferably, the semiconductor material of the substrate of the electrical device of the invention is selected from nanowires and/or nanotubes of carbon, silicon, germanium, alloys of silicon and germanium, and mixtures of such nanowires and/or nanotubes.

However, the semiconductor material of the substrate of the electrical device may also be an organic material selected from a material based on thiophene, such as quaterthiophene and its derivatives such as P3HT (poly-3-hexylthiophene); on pyrrole, such as polypyrrole; on an arylamine, such as triphenylamine, and derivatives thereof, such as poly(triarylamine)s; on heterocyclic macrocycles, such as porphyrins and tetraphenylporphyrin and phthalocyanines and derivatives thereof, such as copper tetraphenylporphyrin and nickel phthalocyanine; on polycyclic aromatic acenes such as pentacene and derivatives thereof, such as triisopropylsilylpentacene; or on arylenes such as pyrene, and its derivatives, such as dicyanoperylenediimide (PDI-$CN_2$).

Preferably, when the semiconductor material of the substrate of the electrical device is an organic material, it is preferably selected from P3HT (poly-3-hexylthiophene), poly(triarylamine)s, anthracene, pentacene, perylene, poly-para-phenylene, poly-para-phenylenevinylene, polyfluorene, and mixtures thereof.

As for the electrodes of the electrical device, in one preferred embodiment, one of them is made of a semiconductor material selected from carbon nanotubes and poly(3,4-ethylenedioxythiophene)/poly(styrenesulfonate).

However, in one particularly preferred embodiment of the invention, the substrate is composed of a silica support covered with a layer of silicon, in which silicon nanowires are etched.

In one likewise preferred embodiment of the apparatus for detecting and/or quantifying mercuric ions $Hg^{2+}$ according to the invention, the at least one compound which complexes mercuric ions $Hg^{2+}$ is grafted onto one of the electrodes of the electrical device.

In one particular embodiment of the apparatus for detecting and/or quantifying mercuric ions $Hg^{2+}$ of the invention, the semiconductor material of the substrate of the electrical device is made of silicon and the at least one compound which complexes mercuric ions $Hg^{2+}$ is grafted onto this semiconductor material by a grafting group selected from an alkyne group, an alkene group, a diazonium group or a triazene group.

In another particular embodiment of the apparatus for detecting and/or quantifying mercuric ions $Hg^{2+}$ according to the invention, the semiconductor material of the substrate of the electrical device is made of silicon covered with a thin oxide layer and the at least one compound which complexes mercuric ions $Hg^{2+}$ is grafted onto this semiconductor material by a grafting group and a silane group, preferably a trialkoxysilane group or a trihalosilane group, more preferably a trimethoxysilane group or a trichlorosilane group.

In yet another particular embodiment of the apparatus for detecting and/or quantifying mercuric ions $Hg^{2+}$ according to the invention, the semiconductor material of the substrate of the electrical device is composed of carbon nanowires and/or nanotubes, and the compound which complexes mercuric ions $Hg^{2+}$ is grafted onto these carbon nanotubes and/or nanowires by a grafting group selected from a diazonium group, a triazene group, a free-radical precursor group, an aromatic or heteroaromatic group, such as a pyrene, anthracene or porphyrin group, or an amine group, or an alcohol group.

According to yet another particular embodiment of the apparatus for detecting and/or quantifying mercuric ions $Hg^{2+}$ according to the invention, one electrode of the electrical device is made of gold, and the compound which complexes mercuric ions $Hg^{2+}$ is grafted onto this electrode by a grafting group selected from an organic sulfur group, preferably a thiol group, a protected thiol group, such as a thioacetate group, or a disulfide group.

In all of the embodiments of the apparatus for detecting and/or quantifying mercuric ions $Hg^{2+}$ of the invention, the at least one compound which complexes mercuric ions $Hg^{2+}$ is dithia-dioxa-monoaza crown ether.

The invention also provides a method for detecting and/or quantifying mercuric ions $Hg^{2+}$, which comprises a step of contacting the sample possibly containing mercuric ions $Hg^{2+}$ with the at least one compound which complexes mercuric ions $Hg^{2+}$ of the apparatus for detecting and/or quantifying mercuric ions $Hg^{2+}$ according to the invention, and a step of reading off the variation in the conduction current measured by the measuring device of the apparatus for detecting and/or quantifying mercuric ions $Hg^{2+}$ of the invention.

The invention will be better understood, and other features and advantages thereof will emerge more clearly, from a reading of the explanatory description which follows.

The invention is based on the finding that the complexation of mercuric ions $Hg^{2+}$ by a compound that complexes mercury, grafted onto a semiconductor material, drastically alters the electrostatic environment of said semiconductor material, producing a change in its conduction properties, which thus allows the electrical detection and/or quantification of the $Hg^{2+}$ ions by transistors or resistors which are functionalized with the compound that complexes mercury.

The compound which complexes mercuric ions $Hg^{2+}$ therefore comprises as its principal entity a group which complexes mercuric ions $Hg^{2+}$, selected from a dithia-dioxa-monoaza crown ether compound, an N,N-di(hydroxyethyl)amine, an N,N-di(carboxyethyl)amine, and mixtures thereof.

This group has a very high selectivity for mercuric ions $Hg^{2+}$.

The compound which complexes mercuric ions $Hg^{2+}$ is bonded, by a grafting group, to part of an electrical device, which may be a purely resistive device or a field-effect transistor device, thereby allowing a readily transportable device to be obtained.

This type of device essentially comprises a substrate comprising at least one part made of a semiconductor material, and two electrodes, which are placed in electrical contact with the semiconductor material, for measuring the variation in the conduction current between these two electrodes when the compound which complexes mercuric ions $Hg^{2+}$ is contacted with mercuric ions $Hg^{2+}$.

The part of the electrical device to which the compound which complexes mercuric ions $Hg^{2+}$ is bonded may be one of the electrodes or the part made of semiconductor material of the substrate of the electrical device of the apparatus for detecting and/or quantifying mercuric ions $Hg^{2+}$ of the invention.

The compound which complexes mercuric ions $Hg^{2+}$ may be bonded to the semiconductor material, or to one of the electrodes, via a grafting group or else by covalent bonding or by weak stabilizing interaction, depending on the semiconductor material or the material of the electrode.

In the invention, however, a bond by grafting of the compound which complexes mercuric ions $Hg^{2+}$ is used, since this type of bond is durable over time and endows the apparatus of the invention with a long lifetime and with enhanced reproducibility and sensitivity.

Where the compound which complexes mercuric ions $Hg^{2+}$ is bonded by grafting, either to the semiconductor material of the substrate of the electrical device, or to the electrode, the compound which complexes mercuric ions $Hg^{2+}$ comprises, further to the aforementioned entity which complexes mercuric ions $Hg^{2+}$, a grafting group selected from a saturated or unsaturated, monocyclic or polycyclic aromatic hydrocarbon group, such as pyrene, an alkene group of vinyl type, an alkyne group, such as an acetylene group, a silane group, for example a trihalosilane group, such as a trichlorosilane group, or a trialkoxysilane group, preferably a trimethoxysilane group, a diazo group, an azide group, a free-radical precursor such as a diazonium group, an isocyanate group, an organometallic group such as, for example, an organolithium group, such as phenyllithium, or an organomagnesium or organozinc group, a sulfur group such as a thiol or disulfide group, a carboxylic acid or a sulfonic acid or phosphoric acid group and their ester derivatives, such as methyl carboxylate, an alcohol group, a phenol group, an amine group, an amide group, or a halide group such as an iodide group.

The term "group of type X" denotes, in the invention, a group comprising a chemical group or a chemical element X.

The grafting group may more particularly be an ethynylphenyl, vinylphenyl, diazophenyl or pyrene group.

More specifically, when the semiconductor material is silicon, the grafting group may be an alkyne group, an alkene group, a diazonium group or a triazene group.

Since silicon is easily oxidizable at its surface, when the semiconductor material is silicon covered with a thin oxide layer, such as the native oxide, for example, the grafting group is preferably a silane group such as a trialkoxysilane group, as for example a trimethoxysilane group, or a trihalosilane group, such as, for example, a trichlorosilane group, or any other species that bonds to the surface of the oxide.

The semiconductor material may be any semiconductor material that will be apparent to a person skilled in the art.

With preference it would be a material made of or based on carbon, silicon, germanium, zinc, gallium, indium, cadmium, or mixtures thereof.

As has already been stated, a "material based on X" denotes, in the invention, a material comprising at least 20 mol % of X relative to the total number of moles present in the material.

The semiconductor material may also be an organic semiconductor material such as oligomers, polymers or small molecules with a mass-average molecular weight of less than 1000 g·mol$^{-1}$, such as pentacene.

For example, the organic semiconductor materials may also be materials based on heterocyclic aromatic compounds, such as thiophene and quaterthiophene and derivatives thereof, such as P3HTs (poly-3-hexylthiophenes); pyrrole, such as polypyrrole; an arylamine, such as triphenylamine, and its derivatives, such as poly(triarylamine)s; heterocyclic macrocycles, such as porphyrins, such as tetraphenylporphyrin, and phthalocyanines, and derivatives thereof, such as copper tetraphenylporphyrin and nickel phthalocyanine; polycyclic aromatic acenes, such as pentacenes, and derivatives thereof, such as triisopropylsilylpentacene; and arylenes, such as pyrene, and its derivatives, such as dicyanoperylenediimide (PDI-CN$_2$).

Examples of such preferred organic semiconductor materials are poly-3-hexylthiophene, poly(triarylamine)s, anthracene, pentacene, perylene, poly-para-phenylene, poly-para-phenylenevinylene, and polyfluorene.

However, the very particularly preferred semiconductor material is composed of silicon nanowires and/or nanotubes and/or of carbon nanowires and/or nanotubes and/or of nanowires and/or nanotubes of a material based on silicon and germanium, such as an alloy with a molar composition $Si_{0.7}Ge_{0.3}$, or an Si/alloy of molar composition $Si_{0.1}Ge_{0.9}$ supernetwork.

By "supernetwork" is meant a nanowire or a nanotube composed, in the direction of its largest dimension, of the repetition of an elementary unit composed of the alternation of an Si layer and a layer made of an alloy of Si and Ge, in this case comprising 10 mol % of silicon, relative to the total number of moles of Si and Ge.

Most preferably, the semiconductor material is composed of silicon nanowires which are etched in a silicon layer on the surface of an insulating material.

This type of material is commonly referred to as SOI, for "silicon on insulator".

The semiconductor material described in the above case is the semiconductor material that constitutes the substrate of the electrical device, in which a change in the conduction properties is induced by the complexing of the $Hg^{2+}$ ions by the compound which complexes mercuric ions $Hg^{2+}$.

In order to be able to measure the conduction properties due to the complexation of the $Hg^{2+}$ ions by the compound which complexes mercuric ions $Hg^{2+}$, electrodes are placed on the substrate made of a semiconductor material as defined above.

The electrodes may be metal electrodes, made for example of gold, silver, palladium, platinum, titanium, doped silicon, copper or nickel.

However, the electrodes may also be made of a semiconductor material such as carbon nanotubes and/or nanowires, or of poly(3,4-ethylenedioxythiophene)/poly(styrenesulfonate), which is a semiconductor polymer.

The compound which complexes mercuric ions $Hg^{2+}$ may also be bonded to one of the electrodes.

It is preferably bonded, as in the case of the semiconductor substrate, by grafting to the material that constitutes the electrode, in which case the compound which complexes mercuric ions $Hg^{2+}$ will further comprise a grafting group as described for the semiconductor material.

The grafting of the compound which complexes mercuric ions $Hg^{2+}$ by the grafting group may be performed in one or more steps.

It is possible, for example, to react the surface of the semiconductor material with a first molecule, and then to react a function of this grafted molecule with a second organic molecule comprising the compound which complexes mercuric ions $Hg^{2+}$.

For example, silicon or its native oxide can be functionalized by a first series of organic molecules, containing terminal functions, to which the molecule which complexes mercury ions is grafted, in a second stage, by conventional techniques of organic, organometallic or inorganic synthesis.

Assemblies produced by covalent bonding or by weak interaction are possible.

For example, an assembly by pi-pi bonding (stabilizing orbital overlap) may be contemplated, preferably when the semiconductor material is composed of carbon nanotubes and/or nanowires.

Still when one or more carbon nanotubes and/or nanowires are used as semiconductor materials, the grafting group may be a triazene group, a free-radical precursor group, as for example a diazonium group, or any molecule which is capable of forming covalent bonds with the carbon atoms, an aromatic or heteroaromatic group, such as a pyrene, anthracene or porphyrin group, or a group derived from the class of the amines allowing noncovalent, i.e., supramolecular, functionalization, an amine group, or an alcohol group, for a reaction with the carboxylic acid groups present on the surface of the carbon nanotubes and/or nanowires, optionally after chemical activation, as for example with a coupling agent, to form esters or amides.

In the case of a semiconductor material based on germanium, the grafting group may be an alkyne or an alkene.

When the semiconductor material is an indium gallium arsenide (InGaAs), the grafting group may be a sulfur group, such as a thiol.

In the case of a semiconductor material based on cadmium and selenium (CdSe) or on cadmium sulfide (CdS), the grafting group may be an amine or sulfur group, such as a thiol.

If the semiconductor material is a zinc oxide, the grafting group may be a carboxylic or phosphoric acid group.

If the semiconductor material is a zinc sulfide (ZnS), the grafting group may be a sulfur group, as for example a thiol group.

In the case of an organic semiconductor material, the compound which complexes mercuric ions $Hg^{2+}$ is integrated during the synthesis of said organic semiconductor material.

When the compound which complexes mercuric ions $Hg^{2+}$ is bonded to one of the electrodes, and the electrode is made of gold, preferably, use will be made for this bonding of an organic sulfur group, such as a thiol group, a protected thiol group, such as a thioacetate group, or a disulfide group, for example.

The grafting group of the compound which complexes mercuric ions $Hg^{2+}$ advantageously comprises, in addition to the grafting group, a spacer moiety, which allows the distance between the compound which complexes mercuric ions $Hg^{2+}$ and the semiconductor material of the substrate or the electrodes to be adjusted.

This spacer moiety may be a $C_1$ to $C_{20}$ alkyl group, which may contain one or more heteroatoms, such as S, O, and N, and/or an aromatic radical, such as a biphenyl radical, or a heteroaromatic radical, such as a thiophene radical.

The device according to the invention is therefore composed:

of an electrical device comprising two electrodes placed on a substrate comprising at least one surface made of an organic or inorganic semiconductor material, and in contact with said semiconductor material, and of a device for measuring the conduction current between the two electrodes, a compound which complexes mercury, selected from a dithia-dioxa-monoaza crown ether compound, an N,N-di(hydroxyethyl)amine, an N,N-di(carboxyethyl)amine, and mixtures of two at least of these compounds, being bonded by grafting to one of the parts of the electrical device that is made of semiconductor material.

This simple structure permits low-cost, large-scale production.

Furthermore, owing to this simple structure, the apparatus of the invention for detecting and quantifying mercuric ions $Hg^{2+}$ can be very small in size, requiring little energy to operate, and this is beneficial to its portability.

The apparatus according to the invention for detecting and/or quantifying mercuric ions $Hg^{2+}$ comprises, in addition to the above-described electrical device, to which at least one compound which complexes mercuric ions $Hg^{2+}$ is bonded, selected from a dithia-dioxa-monoaza crown ether, an N,N-di(hydroxyethyl)amine, an N,N-di(carboxyethyl)amine, or mixtures of these compounds, bonded to the substrate or to one of the electrodes, a device for measuring the variation in the conduction current between the electrodes of the electrical device.

The apparatus for detecting and/or quantifying $Hg^{2+}$ ions may be calibrated such that the conduction current flowing between the two electrodes of the electrical device, and measured by the measuring device, may be connected directly to the concentration of $Hg^{2+}$ ions present in the sample under analysis.

This sample may be a gaseous or liquid sample, especially a water sample.

The simple structure of the apparatus for detecting and/or quantifying $Hg^{2+}$ ions, of the invention, allows low-cost, large-scale production of such an apparatus.

Moreover, owing to this simple structure, the apparatus of the invention can be very small in size, requiring little energy to operate, and this is beneficial to its portability.

To aid understanding of the invention, a description will now be given, purely by way of illustration and without limitation, of exemplary embodiments thereof.

EXAMPLE 1

Transistors-Based Sensor

Apparatus for detecting and quantifying mercuric ions $Hg^{2+}$ were fabricated on SOI (silicon on insulator) where the semiconductor material is an etched silicon nanowire having a width of 280 nm, a length of 4 µm, and a thickness of 16 nm, etched on a 77 nm layer of silicon oxide, in the following way.

1. Synthesis of the Compound which Complexes Mercuric Ions $Hg^{2+}$ with its Grafting Group: N-(4-ethynylphenyl) dithia-dioxa-monoaza Crown Ether.

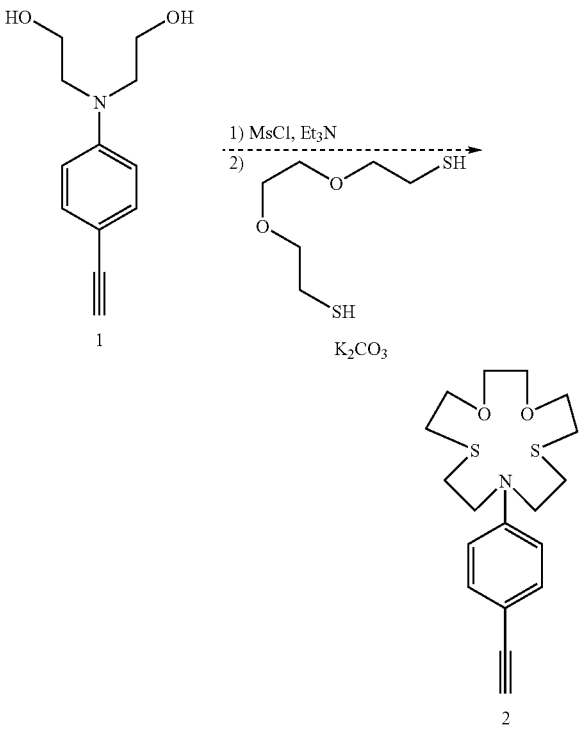

N,N-di(2-hydroxyethyl)-4-ethynylaniline (1) was obtained by the procedure of Fang et al. (Huang J.-H., J. Org. Chem. 2005, 70, 5827-5832). 1 was reacted with methanesulfonyl chloride. The resulting product was then combined with 3,6-dioxa-1,8-octanedithiol and potassium carbonate in accordance with the procedure described by Soto et al. in J. Am. Chem. Soc. 2003, 125, 3418-3419. In accordance with this method, 2 was obtained with a yield of 30%.

2. Grafting of the Compound obtained in the above Step onto the Silicon Nanowire Compound 2 obtained in the step above is grafted onto the silicon nanowire by thermal hydrosilylation. The electrical device is cleaned using a piranha solution (mixture of 3 mol of concentrated sulfuric acid and 1 mol of 30% hydrogen peroxide) and then treated with a 1% HF solution. The activated electrical device is heated at reflux for 2 hours in a 0.5 mM solution of the receptor in mesitylene.

The electrical device is subsequently rinsed with dichloromethane.

3. Test of the Apparatus According to the Invention for Detecting and/or Quantifying Mercuric Ions $Hg^{2+}$ The electrical device obtained in the step above is immersed in a solution containing $Hg^{2+}$ ions at 1 mmol·l$^{-1}$ and then rinsed with deionized water.

It is then dried in air for 5 minutes.

The complexing of the $Hg^{2+}$ ions produces the modification in the conductance of the electrical device.

A relative variation in the conductance $|\Delta g/g|$ of more than 10% but less than 20% was measured.

As is apparent, the apparatus according to the invention for detecting and/or quantifying $Hg^{2+}$ ions exhibits a very high selectivity for $Hg^{2+}$ ions, owing to the selectivity of the compounds which complex mercuric ions $Hg^{2+}$ that are used for its fabrication.

EXAMPLE 2

This example shows that, when one of the compounds which complexes mercuric ions, of formulae 1, 2, and 3 below:

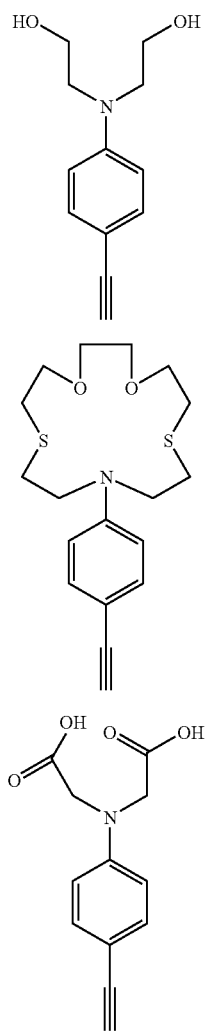

is bonded simply by covalent or other bonds, and not by grafting, the apparatus for detecting and/or quantifying $Hg^{2+}$ ions loses its sensitivity to $Hg^{2+}$ ions in less than 3 months, whereas, when these same compounds are grafted as described in example 1, after 3 months, the apparatus of the invention for detecting and/or quantifying $Hg^{2+}$ ions retains its full sensitivity.

For this purpose, the compounds of formulae 1, 2, and 3, respectively, were applied to the same devices as in example 1, and the relative variation in the conductance $|\Delta g/g|$ was measured after fabrication of the devices and after 1 month, 2 months, and 3 months.

After 3 months, the devices no longer detect $Hg^{2+}$ ions.

In parallel, devices according to the invention in which the compounds of formulae 1, 2, and 3, respectively, were grafted, as in example 1, were also tested right after their fabrication and then after 1, 2, and 3 months. After 3 months, these devices still allow $Hg^{2+}$ ions to be detected and/or quantified with the same sensitivity as right after their fabrication.

EXAMPLE 3

This example shows the synergy effect obtained by grafting two compounds which complex $Hg^{2+}$ ions onto the same device.

For this purpose, a device in which only the compound of formula 1 was grafted was prepared, as in example 1.

For this purpose, N,N-di(2-hydroxyethyl)-4-ethynylaniline (1) was grafted onto the test device by thermal hydrosilylation. The device was cleaned using a piranha solution and then treated with a 1% HF solution. The activated device is heated at reflux for 2 hours in a 0.5 mM solution of the receptor (1) in mesitylene. The device is subsequently rinsed with dichloromethane.

The test device is immersed in a solution containing $Hg^{2+}$ ions at 1 mmol·l$^{-1}$, and then rinsed with deionized water. The device is subsequently dried in air for 5 minutes. The complexing of the $Hg^{2+}$ ions produces a modification to the conductance of the device. A relative variation in the conductance $|\Delta g/g|$ of more than 5% was measured, but less than 10% was measured.

Then, as in example 1, a device was prepared in which only the compound of formula 3 was grafted.

For this purpose, N,N-di(2-carboxyethyl)-4-ethynylaniline (1) was grafted onto the test device by thermal hydrosilylation. The device was cleaned using a piranha solution and then treated with a 1% HF solution. The activated device is heated at reflux for 2 hours in a 0.5 mM solution of the receptor (1) in mesitylene. The device is subsequently rinsed with dichloromethane.

The test device is immersed in a solution containing $Hg^{2+}$ ions at 1 mmol·l$^{-1}$, and then rinsed with deionized water. The device is subsequently dried in air for 5 minutes. The complexing of the $Hg^{2+}$ ions produces a modification to the conductance of the device. A relative variation in the conductance $|\Delta g/g|$ of more than 5% was measured, but less than 10% was measured.

Subsequently, as in example 1, a device was prepared in which the compounds of formulae 1 and 2 were grafted.

For this purpose, N,N-di(2-hydroxyethyl)-4-ethynylaniline (1) and molecule 2 were grafted onto the test device by thermal hydrosilylation. The device was cleaned using a piranha solution and then treated with a 1% HF solution. The activated device is heated at reflux for 2 hours in a 0.5 mM solution of the receptor 1 and 2 in mesitylene. The device is subsequently rinsed with dichloromethane.

The test device is immersed in a solution containing $Hg^{2+}$ ions at 1 mmol·l$^{-1}$, and then rinsed with deionized water. The device is subsequently dried in air for 5 minutes. The complexing of the $Hg^{2+}$ ions produces a modification to the conductance of the device. A relative variation in the conductance |Δg/g| of more than 30% was measured. A synergy effect is observed when these two receptors are grafted jointly.

Then, as in example 1, a device was prepared in which the compounds of formulae 2 and 3 were grafted.

For this purpose, N,N-di(2-hydroxyethyl)-4-ethynylaniline (3) and molecule (2) were grafted onto the test device by thermal hydrosilylation. The device was cleaned using a piranha solution and then treated with a 1% HF solution. The activated device is heated at reflux for 2 hours in a 0.5 mM solution of the receptor (3) and (2) in mesitylene. The device is subsequently rinsed with dichloromethane.

The test device is immersed in a solution containing $Hg^{2+}$ ions at 1 mmol·l$^{-1}$, and then rinsed with deionized water. The device is subsequently dried in air for 5 minutes. The complexing of the $Hg^{2+}$ ions produces a modification to the conductance of the device. A relative variation in the conductance |Δg/g| of more than 20% was measured. A synergy effect is observed when these two receptors are grafted jointly.

The apparatus according to the invention for detecting and/or quantifying $Hg^{2+}$ ions is therefore very sensitive.

The invention claimed is:

1. An apparatus for detecting and/or quantifying mercuric ions $Hg^{2+}$ comprising:
   an electrical device comprising two electrodes and a substrate comprising at least one surface made of an organic or inorganic semiconductor material, the electrodes being in electrical contact with said organic or inorganic semiconductor material, and
   a device for measuring the variation in the conduction current between the two electrodes,
   wherein at least one compound which complexes mercuric ions $Hg^{2+}$, selected from a dithia-dioxa-monoaza crown ether compound, an N,N-di(hydroxyethyl)amine, an N,N-di(carboxyethyl)amine, and mixtures of two at least of these compounds, is grafted onto said semiconductor material or onto an electrode of said electrical device.

2. The apparatus for detecting and/or quantifying mercuric ions $Hg^{2+}$ as claimed in claim 1, wherein the substrate of the electrical device is entirely composed of an organic or inorganic semiconductor material.

3. The apparatus for detecting and/or quantifying mercuric ions $Hg^{2+}$ as claimed in claim 1, wherein the substrate of the electrical device comprises a silica ($SiO_2$) support covered with a semiconductor material.

4. The apparatus for detecting and/or quantifying mercuric ions $Hg^{2+}$ as claimed in claim 1, wherein the semiconductor material of the substrate of the electrical device is selected from a material based on thiophene; on pyrrole; on arylamines and derivatives thereof; on heterocyclic macrocycles and derivatives thereof; on polycyclic aromatic acenes; or on arylenes.

5. The apparatus for detecting and/or quantifying mercuric ions $Hg^{2+}$ as claimed in claim 1, wherein the semiconductor material of the substrate of the electrical device is selected from a material based on one or more of P3HT (poly-3-hexylthiophene), polypyrrole, triphenylamine, polytriarylamine, porphyrins, tetraphenylporphyrins, phthalocyanines, copper tetraphenylporphyrin, nickel phthalocyanine, pentacenes, triisopropylsilylpentacene, pyrene or dicyanoperylenediimide (PDI-CN$_2$), and derivatives thereof.

6. The apparatus for detecting and/or quantifying mercuric ions $Hg^{2+}$ as claimed in claim 1, wherein the semiconductor material of the substrate of the electrical device is selected from poly-3-hexylthiophene, polytriarylamine, anthracene, pentacene, perylene, poly-para-phenylene, poly-para-phenylenevinylene, polyfluorene, and mixtures thereof.

7. The apparatus for detecting and/or quantifying mercuric ions $Hg^{2+}$ as claimed in claim 1, wherein at least one of the two electrodes of the electrical device is made of a semiconductor material selected from carbon nanotubes and poly(3,4-ethylenedioxythiophene)/poly(styrenesulfonate).

8. The apparatus for detecting and/or quantifying mercuric ions $Hg^{2+}$ as claimed in claim 1, wherein the at least one compound which complexes mercuric ions $Hg^{2+}$ is dithia-dioxa-monoaza crown ether.

9. The apparatus for detecting and/or quantifying mercuric ions $Hg^{2+}$ as claimed in claim 1, wherein the semiconductor material of the substrate of the electrical device is selected from a material based on carbon, silicon, germanium, zinc, gallium, indium, cadmium, or mixtures of two at least thereof.

10. The apparatus for detecting and/or quantifying mercuric ions $Hg^{2+}$ as claimed in claim 9, wherein the semiconductor material of the substrate of the electrical device is selected from nanowires and/or nanotubes of carbon, silicon, germanium, alloys of silicon and germanium, and mixtures thereof.

11. The apparatus for detecting and/or quantifying mercuric ions $Hg^{2+}$ as claimed claim 1, wherein the substrate is composed of a silica support covered with a layer of silicon, in which silicon nanowires are etched.

12. The apparatus for detecting and/or quantifying mercuric ions $Hg^{2+}$ as claimed in claim 11, wherein the semiconductor material of the substrate of the electrical device is composed of carbon nanowires and/or nanotubes, and wherein the at least one compound which complexes mercuric ions $Hg^{2+}$ is grafted onto the semiconductor material by a group selected from a diazonium group, a triazene group, a free-radical precursor group, an aromatic or heteroaromatic group, or an amine group, or an alcohol group.

13. The apparatus for detecting and/or quantifying mercuric ions $Hg^{2+}$ as claimed in claim 11, wherein the semiconductor material of the substrate of the electrical device is composed of carbon nanowires and/or nanotubes, and wherein the at least one compound which complexes mercuric ions $Hg^{2+}$ is grafted onto the semiconductor material by one or more of a pyrene, anthracene or porphyrin group.

14. The apparatus for detecting and/or quantifying mercuric ions $Hg^{2+}$ as claimed in claim 1, wherein the at least one compound which complexes mercuric ions $Hg^{2+}$ is grafted onto the semiconductor material of the substrate of the electrical device.

15. The apparatus for detecting and/or quantifying mercuric ions $Hg^{2+}$ as claimed in claim 14, wherein the semiconductor material of the substrate of the electrical device is silicon and wherein the at least one compound which complexes mercuric ions $Hg^{2+}$ is grafted onto the semiconductor material by a grafting group selected from an alkyne group, an alkene group, a diazonium group or a triazene group.

16. The apparatus for detecting and/or quantifying mercuric ions $Hg^{2+}$ as claimed in claim 14, wherein the semiconductor material of the substrate of the electrical device is silicon covered with an oxide layer and wherein the at least one compound which complexes mercuric ions $Hg^{2+}$ is grafted onto the semiconductor material by a grafting group selected from a trialkoxysilane group or a trihalosilane group, a trimethoxysilane group, or a trichlorosilane group.

17. The apparatus for detecting and/or quantifying mercuric ions $Hg^{2+}$ as claimed in claim 1, wherein the at least one compound which complexes mercuric ions $Hg^{2+}$ is grafted onto one of the electrodes of the electrical device.

18. The apparatus for detecting and/or quantifying mercuric ions $Hg^{2+}$ as claimed in claim 17, wherein said electrode onto which the compound which complexes mercuric ions $Hg^{2+}$ is grafted is made of gold and wherein the at least one compound which complexes mercuric ions $Hg^{2+}$ is grafted onto the electrode by a grafting group selected from a thiol group, a protected thiol group, a thioacetate group, or a disulfide group.

19. A method for detecting and/or quantifying mercuric ions $Hg^{2+}$, which comprises the following steps:
 a) contacting a sample possibly containing mercuric ions $Hg^{2+}$ with at least one compound which complexes mercuric ions $Hg^{2+}$ of the apparatus comprising:
  an electrical device comprising two electrodes and a substrate comprising at least one surface made of an organic or inorganic semiconductor material, the electrodes being in electrical contact with said organic or inorganic semiconductor material, and
  a device for measuring the variation in the conduction current between the two electrodes,
 wherein the at least one compound which complexes mercuric ions $Hg^{2+}$, selected from a dithia-dioxa-monoaza crown ether compound, an N,N-di(hydroxyethyl)amine, an N,N-di(carboxyethyl)amine, and mixtures of two at least of these compounds, is grafted onto said semiconductor material or onto an electrode of said electrical device, and
 b) reading off the variation in the conduction current measured by the measuring device of the apparatus.

* * * * *